(12) United States Patent
Eid et al.

(10) Patent No.: US 11,471,149 B2
(45) Date of Patent: Oct. 18, 2022

(54) SUTURE-MATERIAL-HANDLING DEVICE AND SYSTEM FOR PRODUCING A SUTURE KNOT

(71) Applicant: Intrasoft AG, Hünenberg (CH)

(72) Inventors: Karim Eid, Zürich (CH); Benjamin Ebner, Göhrwihl (DE); Enea Martinoli, Locarno (CH); Antonello Zuddas, Neuhausen (CH); Stefan Hofstetter, Baar (CH); Ugur Bastas, Hünenberg (CH)

(73) Assignee: INTRASOFT AG, Hünenberg (CH)

( * ) Notice: Subject to any disclaimer, the term of this patent is extended or adjusted under 35 U.S.C. 154(b) by 285 days.

(21) Appl. No.: 16/348,973

(22) PCT Filed: Oct. 24, 2017

(86) PCT No.: PCT/EP2017/077194
§ 371 (c)(1),
(2) Date: May 10, 2019

(87) PCT Pub. No.: WO2018/086879
PCT Pub. Date: May 17, 2018

(65) Prior Publication Data
US 2019/0269398 A1    Sep. 5, 2019

(30) Foreign Application Priority Data
Nov. 11, 2016  (EP) ..................... 16198466

(51) Int. Cl.
*A61B 17/04* (2006.01)
*A61B 17/062* (2006.01)
*A61B 17/06* (2006.01)

(52) U.S. Cl.
CPC ...... *A61B 17/0469* (2013.01); *A61B 17/0625* (2013.01); *A61B 2017/0472* (2013.01);
(Continued)

(58) Field of Classification Search
CPC ............ A61B 17/0469; A61B 17/0625; A61B 2017/0472; A61B 2017/06042; A61B 2017/0608; A61B 2017/06076
See application file for complete search history.

(56) References Cited

U.S. PATENT DOCUMENTS

| | | |
|---|---|---|
| 2013/0158567 A1 | 6/2013 | Levin et al. |
| 2014/0163583 A1 | 6/2014 | Rush et al. |
| | (Continued) | |

FOREIGN PATENT DOCUMENTS

| | | |
|---|---|---|
| AT | 166938 B | 10/1950 |
| EP | 2392265 A1 | 12/2011 |

OTHER PUBLICATIONS

International search report for patent application No. PCT/EP2017/077194 dated Jan. 8, 2018.

*Primary Examiner* — Melanie R Tyson
(74) *Attorney, Agent, or Firm* — Bachman & LaPointe, P.C.

(57) ABSTRACT

A suture-material-handling device includes a suturing head having first and second jaw sections, which can move relative to each other, and a first needle element associated with the jaw sections and designed to perform a first piercing and thread bring-along operation of a first thread end of the thread in a closed relative position of the jaw sections. A second needle element associated with the suturing head can be actuated separately from the first needle element and is adjacent to the first needle element. The second needle element is designed to perform a second piercing and thread bring-along operation for the second thread end of the thread in the closed relative position of the jaw sections. The second thread end is opposite the first thread end, and in order to perform locally spaced apart and consecutive double piercing of a suture carrier, the second needle ele-
(Continued)

ment is designed to perform a pivoting and/or curved motion that brings along the second thread end.

20 Claims, 3 Drawing Sheets

(52) U.S. Cl.
CPC ............... *A61B 2017/0608* (2013.01); *A61B 2017/06042* (2013.01)

(56) References Cited

U.S. PATENT DOCUMENTS

2014/0296880 A1* 10/2014 Heneveld ........... A61B 17/0469
606/144
2014/0316443 A1  10/2014 Fanton et al.

* cited by examiner

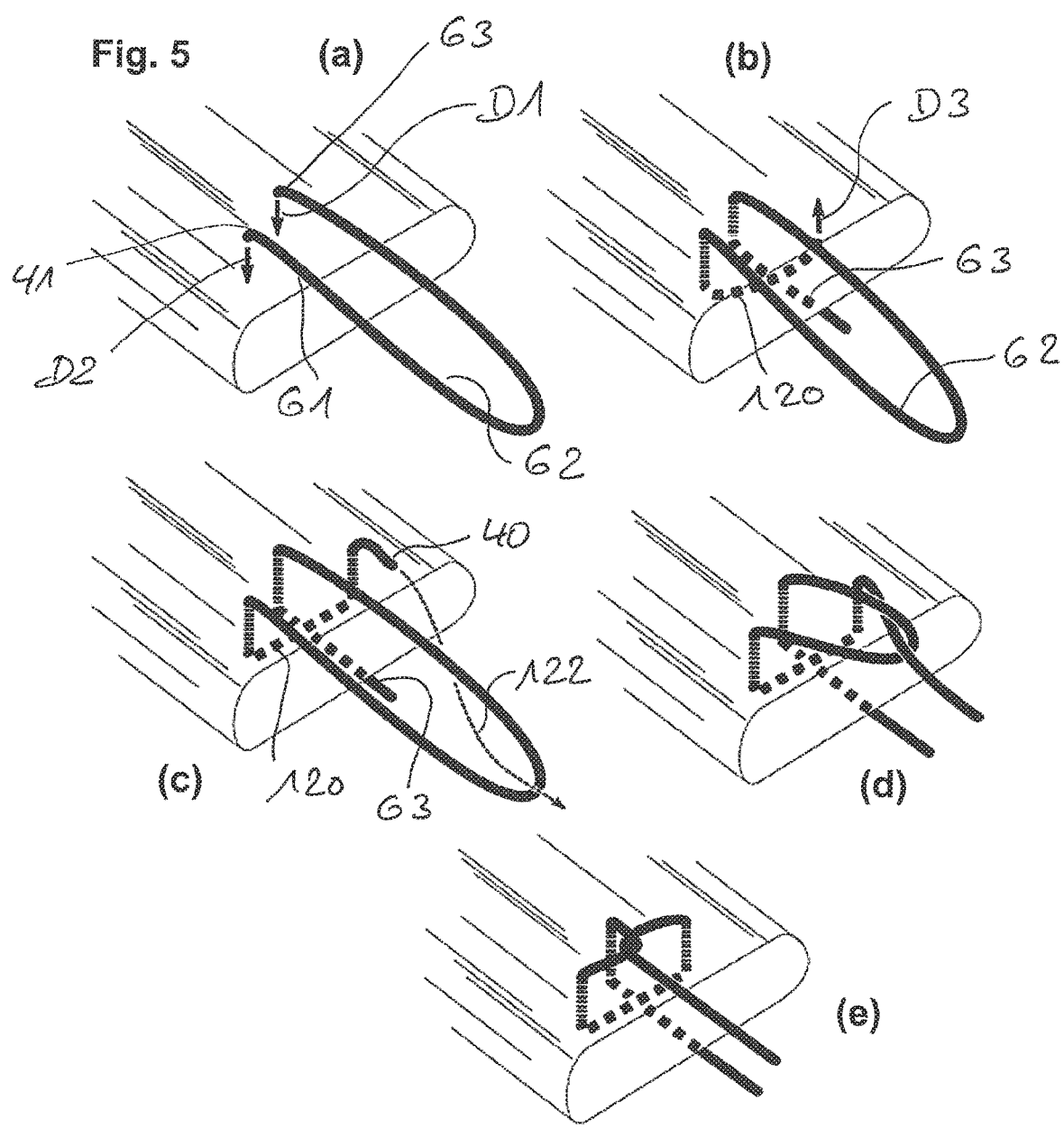
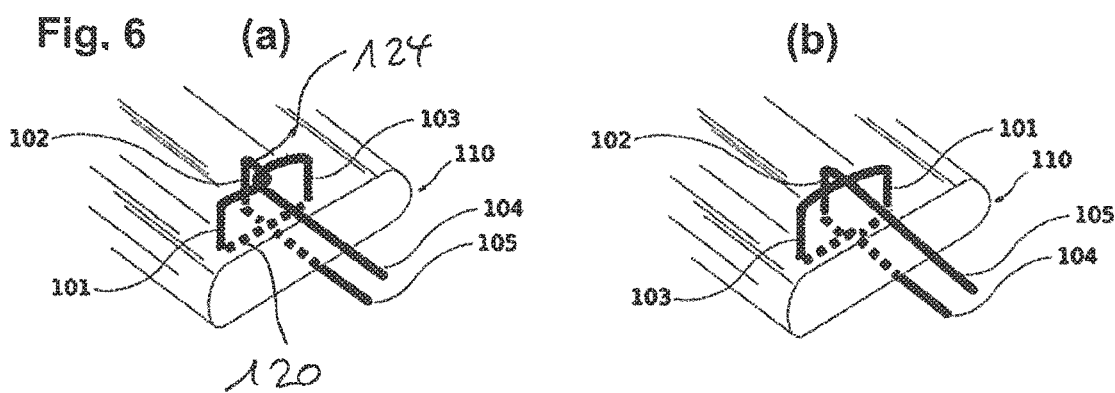

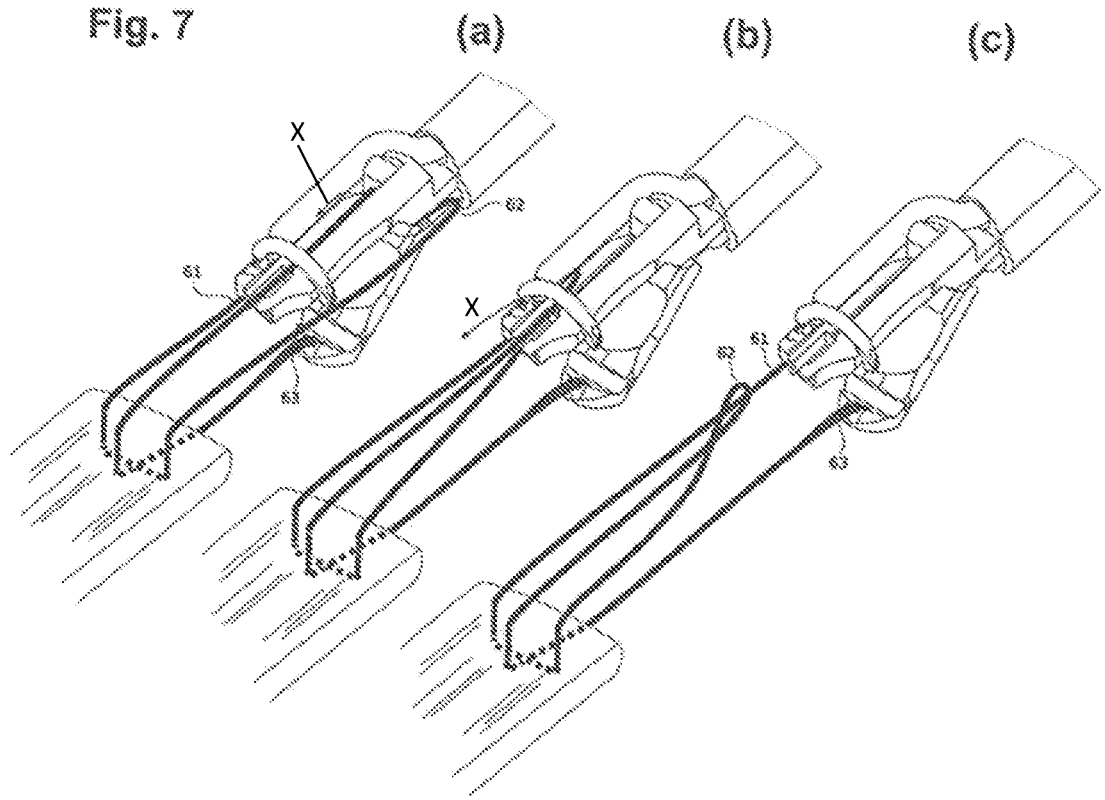
Fig. 7 (a) (b) (c)
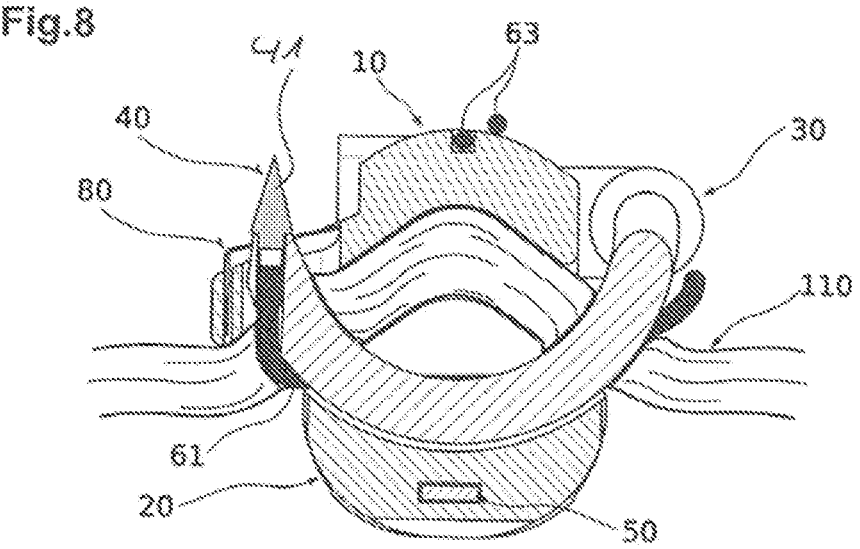
Fig. 8

SUTURE-MATERIAL-HANDLING DEVICE AND SYSTEM FOR PRODUCING A SUTURE KNOT

BACKGROUND OF THE INVENTION

The present invention relates to a suture material handling device. The present invention further relates to a system for producing a suture knot in a suture carrier, wherein such a system has in particular a suture material handling device.

Generic suture material handling devices are well known from the prior art and are used for numerous application purposes, in the case of a which a thread (which typically consists of a surgical suture material) has to be transferred into a suture or a knot, respectively. Such a generic suture material handling device is known from EP 2 392 265 B1 in the form of a suturing apparatus, which comprises suturing head, which has a first and a second jaw section and which can be actuated by means of a suitable hand section. The jaw sections can be moved relative to one another, whereby such an arrangement is suitable in particular to grip for instance a section, which is to be provided with the suture, of a biological material by means of the jaw sections at or on the suture carrier, respectively, in order to then provide this suture carrier with a suture, which is to be realized with the thread. Concretely, EP 2 392 265 B1 teaches, for instance, that the two jaw sections can access a first or (opposite) second flat side, respectively, of the suture carrier in particular by means of manual actuation, and first needle elements in the form of a bendable needle then grip from a first one of the jaw sections through the suture carrier material into the second one of the jaw sections, thereby piercing the suture carrier and can subsequently be retracted back into an initial position again. The described prior art thereby provides that in response to one of the two relative motions, suitable entrainers, which are provided on the needle elements, can entrain a thread, which is guided on one of the jaw sections, whereby this preferably takes place by means of a slit formed in a needle end of the needle elements.

A single suture can then be produced in this way in that the piercing and entraining motions of the needle elements are performed by a suitable operating person, for instance an operator, after the gripping of the suture carrier by means of the jaw sections, which are preferably designed to be pivotable in a pincer-like manner.

In particular in the case of more complex demands on the attaching of a suture material thread to an (in particular biological) suture carrier, however, such an approach is not sufficient to produce a suture, which is stable and which is in particular protected against unintentionally ripping out. For instance using the example of a tendon (torn from a bone) as biological material, the tendon end of which, which is to be provided with suture material, is understood to be a suture carrier, such an approach by introducing an individual suture or a plurality of adjacent single sutures is not sufficient, so that either lengthy healing processes without extensive suture support have to be accepted or an operator has to provide more complex knot patterns by hand and without extensive equipment support—with the corresponding operational effort.

SUMMARY OF THE INVENTION

It is thus the object of the present invention to improve a suture material handling device with regard to the support of more complex suture and bone structures, which can be created or supported, respectively, by means of such a device, thereby in particular to provide for the introduction of a more complex suture or knot structure, respectively, which is improved with regard to a hold on the suture carrier, a risk of an unintentional tearing off or tearing out, respectively, as well as a mechanical strength. Even though a fastening of the thread to or in a suture carrier, respectively, which is made from biological material, is preferred thereby, it is not to limit the field of application of the invention.

The object is solved by means of the suture material handling device comprising the features disclosed herein as well as the system for producing a suture knot also as disclosed herein. Advantageous further developments of the invention are described in the respective subclaims, whereby structural further developments of the respective subject matters of the invention are to also be considered as belonging to the invention for the respective other subject matter of the invention, and subclaims of the system further develop the handling device according to the invention and vice versa in this respect. Method aspects, which follow in particular from a handling or an operation, respectively, of the suture material handling device according to the invention as well as from a handling or an operation, respectively, of the system for producing a suture knot in a suture carrier according to the invention, are to also be considered as being disclosed according to the invention as part of the present invention, so that such an operating method is to also be considered as being disclosed according to the invention.

The suture material handling device additionally associates second needle elements with the first needle elements adjacent to the latter in an advantageous manner according to the invention, wherein said second needle elements are broadened with regard to their functionality as compared to the first needle elements (known from the generic prior art): This is so, because said second needle elements are not only designed to produce a second piercing as well as thread entraining operation for a second thread end opposite to the first thread end of the (individual) thread when the jaw sections are suitably closed or are in the relative position moved toward one another. The second needle elements are also provided according to the invention for performing out a double piercing of the suture carrier, so that, in combination with the functionality of the first needle elements, a total of (at least) three piercing operations can be performed out on the suture carrier, adjacent to one another. For this purpose, the second needle elements have an entraining section, which does not only entrain the second thread end for piercing for the consecutive two piercing operations, this entraining section according to the invention is also designed to carry out a pivoting or curved motion, respectively, of the second thread end, in particular between the consecutive piercing operations.

With this, the invention then does not only make it possible to perform a plurality of piercing operations on or in the suture carrier, respectively, but a transverse connection (which can then be suitably tightened or is to be tightened, respectively) on the respective surface of the suture carrier is also designed by the pivoting or curved motion, respectively, according to the invention, realized by means of the entraining section, which is designed to be suitably pivotable, which transverse connection, in addition to the actual piercings, provides for additional strength, in combination with material protection, and thus enable the object according to the invention of a firm, simultaneously tear out-proof and gentle suture (suture knot or knots, respectively).

This effect also follows in particular from the independent system, which, according to preferred embodiment of the invention, combines a suture material handling device as disclosed herein (which is claimed as such and without a thread) with a corresponding thread having the first or second thread end, respectively, but the system according to the invention in particular also realizes the invention independently.

It is provided as essential mechanical-structural component of the invention for embodying the entraining section (handling device) according to the invention or the thread guide and corresponding thread deflecting elements (system), respectively, that the second needle elements have a curve shank, which is preferably arcuately curved and which forms a needle section on the end side as well as the entraining section for releasably inserting the second thread end. This needle section can thereby in particular also be realized by the second thread end itself, namely in that a thread end, which is suitably provided with a (preferably rigid) needle on this second end, is inserted into the entraining section according to the further development and thus realizes the needle section of the second needle elements.

According to the invention forming an additional further development, these second needle elements are then provided on the end side of a shank assembly, which can preferably be manually rotated and which is mounted on the suturing head, wherein, in a particularly preferred embodiment, this rotatable mounting takes place in one of the jaw sections. This shank assembly can then be set into rotation (forward as well as return rotation) via the handling section, which is suitably associated with the suturing head, in otherwise known manner, for instance by means of a suitably actuatable lever, in order to effect the operation according to the invention of the second needle elements (first piercing, pivoting or curved motion, respectively, and opposite the second piercing with regard to the surfaces of the suture carrier, which are to be pierced, then return motion).

It is additionally structurally advantageous to design this shank assembly so as to be deflected or cropped, respectively, at a transition section eccentrically to the second needle elements, so that the pivoting or rotational motion, respectively, according to the invention of the second thread end is ensured in an elegant manner and with little mechanical-structural effort in this respect.

While it is also particularly preferred as a further development to associate a guide and receptacle for the first thread end (which, according to a preferred implementation as part of the system is designed in a loop-like manner and which provides, for instance, analogously to the approach according to EP 2 392 265 B1, the entraining by means of the first needle elements in combination with a piercing operation, which is to be performed by means of these needle elements) with one of the jaw sections, it is favorable as part of the invention to provide the thread end receiver elements according to the further development for the second thread end adjacent to this guide or receptacle, respectively, of the first thread end. In the implementation according to the invention, this then has the result that after the first piercing operation according to the invention, the pivoting or curved operation, respectively, and second piercing operation of the second thread end in each case, the latter can be suitably deposited (more preferably snap-fastened or snap-locked, respectively) at or in the thread end receiver element, respectively, so that the second needle elements can then be moved back without attached second thread end. This particularly preferred embodiment then has the result that in response to a subsequent release of the jaw sections from the suture carrier and a removal of the suturing head from the suture carrier, a tensile force is introduced into the second thread end via this thread end receiver element, which then provides for the tightening of the thread and thus the completion of the complex suture or knot structure, respectively.

The term of the flat side of the suture carrier is to thereby be interpreted broadly and is in particular not limited to a plane or flat side, in fact, that surface section of the suture carrier, which—deformed or undeformed—allows for the introduction of the piercings according to the invention, is also considered to be the proper flat side.

It becomes clear that in the elegant interaction between the pair of the jaw sections and the guide and movement of the first and second needle elements realized thereon or thereby, respectively, these operations, which are necessary for the production of the complex knot structure, can be effectively performed or supported, respectively; a sliding section provided according to a further development on the jaw section located opposite the second needle elements thus ensures that the pivoting or curved motion, respectively, of the second needle elements is supported in the best possible manner, without surrounding tissue being damaged or resulting in other disadvantages, for instance during an operation.

As a result, the invention thus makes it possible to provide a complex suture structure on or in a (preferably biological) suture carrier in a surprisingly simple and elegant manner, which provides for three adjacent piercings as well as for two transverse loops, which are tightened in a web-like manner and which connect these piercings, preferably on opposite sides. The result is a highly stable, tissue-friendly suture structure (knot structure), which is similar to the so-called Mason-Allen suture structure, which is known from the medical literature, but without it having to be performed purely manually in a complex manner by a correspondingly trained operator. The advantages of time savings, a lowering of the education and training effort for operators and increase of the quality of the created suture resulting therefrom for the medical practice (but not only for the latter) are obvious, so that the present invention has the potential like never before to use complex, mechanically stable and tissue-friendly suture structures in order to connect a suture material thread to a suture carrier. Last but not least, the present invention has advantages for endoscopic surgical procedures as well as for instance for the arthroscopy.

While the present invention is also particularly preferably realized as medical or surgical instrument, respectively (or as system having such an instrument, respectively, in combination with a suture material) and is provided in a suitable manner with a handling or operating section, respectively, on the suturing head for the (preferred) manual actuation, the present invention is nonetheless not limited to this application. In fact, it also lends itself to use or to geometrically further scale down, respectively (and in particular to then also actuate or control, respectively, via remote-controlled or endoscopic aggregates, respectively) with regard to micro-invasive applications, for instance, and, as is alternatively also captured in the principle of further developments of the invention, to equip it for textile, plant-based, plastic or other suture carriers, in the case of which the discussed advantages of the suture, which can result, can likewise be realized in a simple manner.

BRIEF DESCRIPTION OF THE DRAWINGS

Further advantages, features and details of the invention follow from the following description of preferred exemplary embodiments as well as on the basis of the drawings, in which:

FIG. 5 shows, with partial illustrations (a) to (e), production steps for producing a complex suture or a complex suture knot, respectively, from the thread by hand actuation of the suture material handling device according to one of claims 1 to 4, thus corresponding to the functionality of an exemplary embodiment of the system according to the invention;

FIG. 6 shows, in partial images (a) and (b), views of a completed suture after a removal of the suture material handling device from an engaged position on the suture carrier;

FIG. 7 shows, with partial illustrations (a) to (c), details of a thread handling after the completion of the piercings, thus according to a detailing of the functionality of the suture material handling device or of the system according to the invention, respectively, between the method steps (c) and (d) in FIG. 5, and FIG. 8 shows a detail cross sectional illustration through the suture material handling device or the system, respectively, in the shown exemplary embodiment in response to the operation of the second needle elements after rotation thereof has occurred.

DETAILED DESCRIPTION

Figure 1:
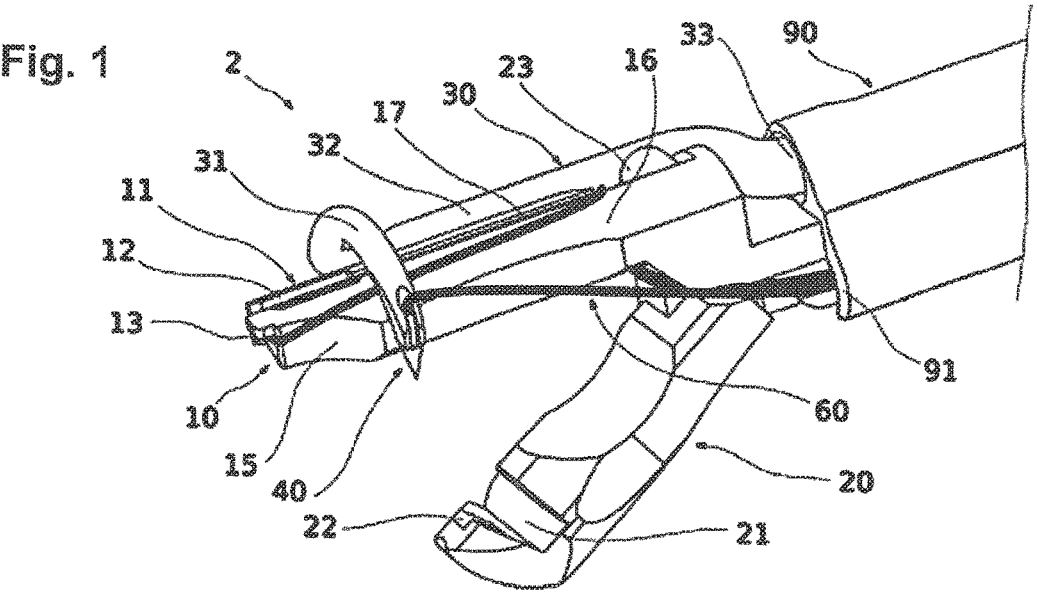
FIG. 1, FIG. 2 show perspective views of the suture material handling device according to a first exemplary embodiment of the invention in the open position, i.e. not located at an engaged position on a suture carrier, with inserted thread.

The illustrations of FIGS. 1 to 4 illustrate the mechanical-structural implementation of a suturing head as part of the shown suture material handling device or of the system of this first exemplary embodiment realized therewith, respectively. A pair of jaw sections consisting of a lower jaw section 20 and an upper jaw section 10 is connected to one another in a pincer-like manner by means of a pivot joint 24 so as to be pivotable against one another. The illustrations of FIG. 1, FIG. 2 thus show an open position of these jaw sections, wherein these jaw sections can then be brought in an engaged position for interacting with a suture carrier, which is shown here as schematic muscle section 110, in such a way that the upper jaw section 10 as well as the lower jaw section 20 can lie on a corresponding upper or lower flat side, respectively, of this suture carrier. For this purpose, the jaw sections move relative to one another, wherein in particular the lower jaw section 20, acting on a jaw arm 23 by means of actuating elements, which are not shown in detail, can perform a pivot motion closing them. In an actuating or handling section 90, respectively, which is only shown schematically, suitable actuating elements are associated with the jaw section 20 and are guided in a housing or below a cover 91, respectively.

Figure 4:
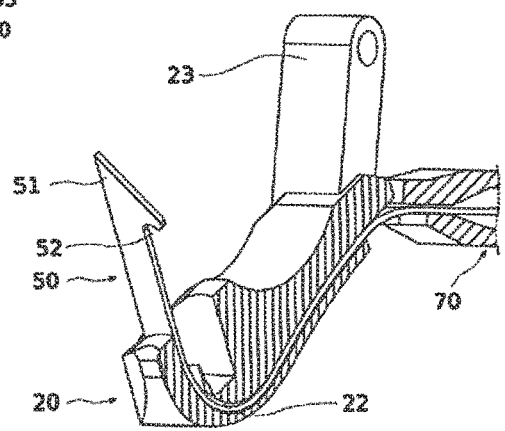
FIG. 4 shows a detail sectional view of the lower jaw section in the exemplary embodiment of FIGS. 1 to 3 with first needle elements guided therein.

The lower jaw section 20, which is illustrated in a pivotable manner by means of an assembly 70, see in particular the detail view of FIG. 4 illustrated in the longitudinal section, has a channel 22, which extends along the extension of the jaw section and which is curved upwards in the direction of an engagement-side (front-side or distal, respectively) end, so that a flat needle 50 guided in this channel 22 can escape upwards from this engagement-side end, i.e. in the direction of the opposite second jaw section 10.

In this way, the lower jaw section comprising the curved or bent guide 22, respectively, provided therein for the bendable flat needle 50 generally realizes a teaching described in EP 2 392 265 B1 for the prior art, namely the option of guiding the needle 50 with its tapered needle end 51 from the engaged position of the lower jaw section 20 from below through the suture carrier (and back again) in the manner, which will be described in detail below; this movement of the needle occurs with the help of a non-illustrated actuating unit, which is provided on the rear (proximal) end of the jaw section and which, for instance clamping the needle 50, can exert a pushing and pulling motion on the needle 50, which moves the needle end 51. In addition, the needle 50 has a protrusion or hook section 52, respectively, which serves as entrainer in the manner, which will be described below, for receiving and entraining a thread end (here of the first thread end 63) of the thread 60 shown in FIG. 3.

Figure 2:
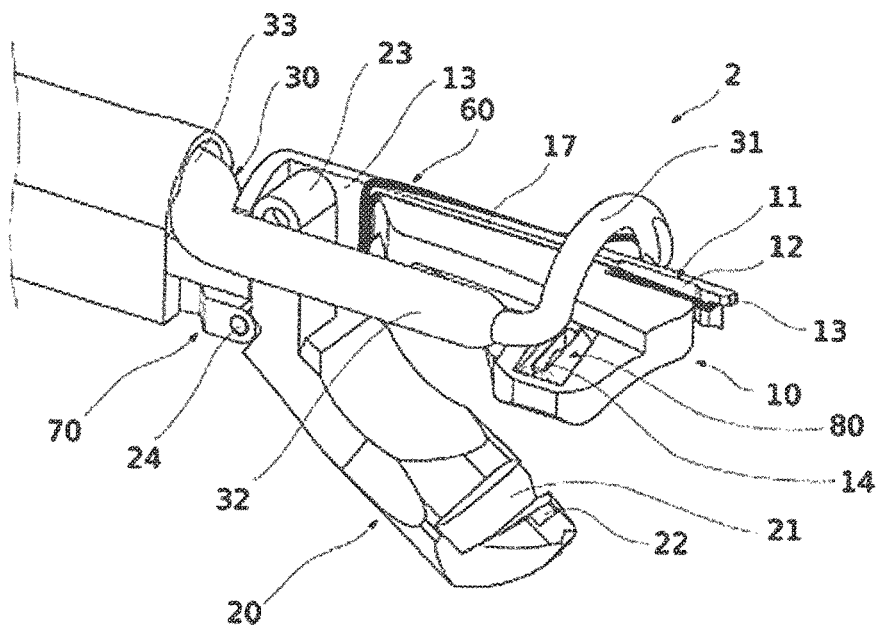
Figure 3:
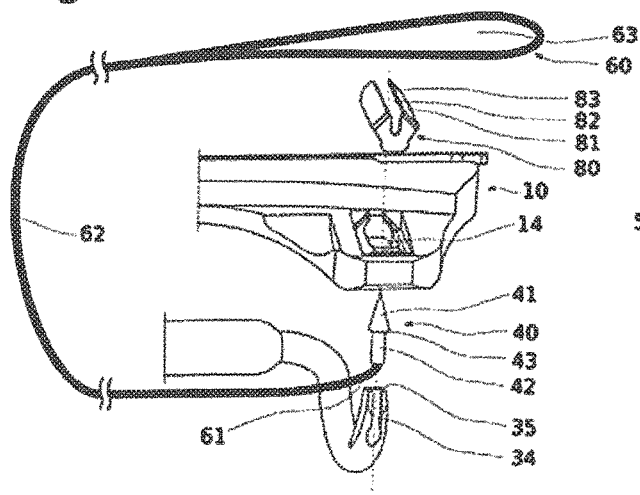
FIG. 3 shows a schematic exploded illustration of a jaw section as well as of the second needle elements according to exemplary embodiment of FIGS. 1, 2 with thread, which is related thereto in a schematic manner.

The upper jaw section 10 shown in FIGS. 1 to 3 has an elongated carrier 16, on which, in the initial state, namely when the thread 60 is not yet introduced into or into the suture carrier, respectively, said thread is held. In this preparation state of the device, the thread 60 extends, more specifically, with its first end 63, which is designed in a loop-shaped manner, from a guide section 17 of the carrier 16 associated therewith, is guided downwards at a proximal end (rearward based on the suture carrier), and is then received with its second thread end 40, which is located opposite the first end 63, by a second needle unit or element 30, which, adjacent to a cropped arm section 32, leads into a curve shank 31 on the end side, which, in turn, has a receiving slit 34 on its outer end 35 for inserting the second thread end 40. More specifically, the second thread end 40 is designed such that the end-side thread section 61 of the thread 60 leads into a needle tip 41, adapted to the slit 34 via a cylindrical shank section 42, so that, in the inserted state of the second needle end 40 into the front end 35 of the second needle element 30, the latter are designed on the end side for performing further piercing operations of the suture carrier 110, as will likewise be described below.

As follows in particular from the illustrations of FIG. 1, FIG. 2, the cropped arm or shank section 32, respectively, of the second needle element 30, in the direction of the handling or operating unit 90, respectively, is designed in the manner of a shaft 33, which is rotatably mounted therein, wherein, even farther to the rear and not shown in the Figures, handling or rotating elements, respectively, are then associated with this shaft such that a rotation around the axis of rotation 33 can be effected, so that a pivoting the cropped shank or arm section, respectively, as well as of the curve shank 31 distally provided thereon is effected with end-side needle 41. It can also be seen that this rotation or pivoting operation, respectively, takes place around the carrier section 16 of the upper jaw section 10.

It is thus made possible with this structure that the curve shank 31 (initially with needle 40 held therein) performs a pivot-like or curved motion, respectively, in response to rotation around the shaft 33, whereby the jaw sections are typically moved relative to one another in the case of this operating state and are thus closed. In this operating state, a guide slit 21, which is provided in the lower jaw section 20 and which runs at right angles to the direction of extension (and thus at right angles to the direction of extension of the elongated carrier 16) then engages with the needle tip 41, so that the latter can glide on or in the slit 21, respectively, and an impact of surrounding tissue or the like at a medical intervention site is thus in particular effectively avoided. In addition, the slit 21 facilitates the creation of the re-piercing.

In particular the views of FIGS. 2 and 3 additionally show a needle or thread entrainer, respectively (thread end receiver element) in the form of the assembly 80, which are inserted into an aperture 14 of the upper jaw section 10 and which have a pair of legs 81, which can be moved against one another, which, forming respective edges 83, are arranged so as to be located opposite one another at a slit opening 82. The assembly 80, suitably adapted to the needle end 41 or the corresponding needle shank 42, respectively, is designed to snap-lock this needle end as soon as the needle end located on the front (distal) end of the curve arm 31 (here from below) reaches the jaw section 10 at the end of the pivoting motion performed by the needle element 30, and enters into the assembly 80. By snapping the jaw sections 81 with the ledge formed between the needle tip 41 and the shank 42 of the second thread end, it then allows for a retracting (opposite) pivoting motion of the element 30, to remove this needle end from the curve shank 31, so that it remains in the receptacle in the upper jaw section 10 formed by the assembly 80.

An opening 12, which, as part of the guide 11, which holds the first (loop-shaped) thread end 63, is designed in a slit-like manner and for engaging through or interacting with, respectively, the needle end 51 of the first flat needle element 50, is designed approximately adjacent to this section 14 in the upper jaw section 10 in the edge-side thereof. More precisely, the illustrations of FIG. 1, FIG. 2 show the operating state of the thread held on the guide 11 (more precisely: the thread loop 63 as first thread end), wherein an end-side protrusion 13 additionally prevents a slipping of this thread loop to the top in this regard. In interaction of the first flat needle element 50 with the thread end receiver guide 11 and in the case of closed jaw sections 10, 20, the needle 50 is able to engage with its engagement-side needle end 51 through the opening slit 12 from the bottom to the top, thereby moves a section of the thread loop 63 across the triangular tip end 51 (FIG. 4), so that the lateral hook or protrusion section 52, respectively, can entrain the loop 63 in response to a subsequent pull-out of the needle 50 by means of pulling of the pusher unit 70 (thus according to a downwards motion of the needle section 51), and can thus then also effect a thread transport through the suture carrier 110. In the state of the needle 50, which is then retracted, in the jaw section 20, the hook 52 also ensures a favorable holding or clamping effect, respectively, of the entrained thread in the jaw section (for instance with respect to a theoretically conceivable slit).

The illustrations of FIGS. 5 and 6 describe this mechanical functionality and structure of the suture material handling device (more precisely: of the suturing head of FIGS. 1 to 3), together with the movements, which the thread 60 performs in response to these handling steps, FIG. 5 thus describes the operation or the effectiveness, respectively, of the system according to the invention in interaction between suture material handling device and thread 60, which is initially received therein and which is later brought onto or into the suture carrier 110, respectively.

The sequence of the handling steps of the thread 60 shown schematically in FIG. 5 initially requires that the upper jaw section 10 and the lower jaw section 20 access the thread end 110 shown in FIG. 5 as suture carrier from the top (10) or from the bottom (20), respectively, in the above-described manner. The introduction of two piercings D1 and D2 with respective corresponding thread ends 63 (for D1) or 41 (for D2), respectively, thus initially takes place from this position. The partial image in FIG. 5 (a) assigns arrows to these piercing operations in each case, wherein the piercing D1 takes place in the above-described manner by means of the suture carrier 110 from its upper side shown on the top in the Figures (thus according to the side of the upper jaw section 10) through the carrier material to the underside thereof. Due to the effect of the first needle elements (flat needle 50), initially from the direction of the lower jaw section 20, the carrier material 110 is thereby pierced from bottom to top, the hook section 52 of the needle 50 then grips the thread end 63 in the above-described manner and pulls it downwards according to the marking for the piercing D1.

To produce the second piercing D2, the second needle element 30 moves with front curve shank 31 and second thread end located therein by means of needle end 41 from the position shown in FIG. 1, FIG. 2, and pierce the carrier material of the suture carrier 110, again from top to bottom, thereby entraining the needle end 41. At the end of this operation, the loop shown in FIG. 5 (a) is created, which is essentially formed by a thread intermediate section 62, which connects the first thread end 63 and the second thread end 40. The order of these piercings is not important, the piercing D1 can in fact also occur after the piercing D2, even after the piercing D3, which will be described below.

A further pivoting of the second needle element 30 comprising end-side curve shank 31 (with needle 41 still sitting therein) has the result that the second suture end forms a web-like suture section 120, which runs at right angles (shown by means of dashes) on the underside of the suture carrier, namely until, in response to the further (rotational) pivoting of the curve shank 31, the end thereof, i.e. the needle 41 sitting therein as second thread end reaches the lower surface on the lower flat side of the suture carrier again. A further rotation or pivoting, respectively, then creates a third piercing through the carrier 110, this time directed upwards, according to the arrow illustration D3 (partial image FIG. 5 (b)), so that the thread end 40 (or the needle 41 realizing the latter, respectively), escapes at the end of this piercing in the upward direction and out of the upper side of the suture carrier 110. The partial illustration of FIG. 5 (b) makes it clear, how the first thread end (loop 63) points to the free end of the suture carrier 110, it is likewise illustrated in a dashed manner, because it runs below this carrier.

At the end of the piercing D3, partial Figure (b), the needle tip 41, together with shank 42, also reaches the assembly 80, which acts as thread end receiver element, as described above. More precisely, the needle tip 41 engages through the slit-like opening 82 formed between the jaw pair 81 and latches therein, when the opposite rotary or rotational movement, respectively, of the second needle element 30 (together with the curve section 41 moved therewith), which now takes place, is moved opposite the arrow direction according to D3. This has the result that the second thread end 40 with attached needle 41 becomes disengaged from the slit-shaped receiving area 34 of the curve shank 31, and that the needle element 30 thus transfers the second thread end 40 to the entraining elements of assembly 80 in the front-side end 14 of the upper jaw section 10.

At the time of the actuating operation according to partial image (c) in FIG. 5, the person operating the suture material handling device (thus, e.g., the operator) releases the jaw pair 10, 20 from its contacting engaged position on the carrier 110, so that a tensile force is likewise exerted on the suture ends 63, 41 with the removal of the handling device from the carrier, and the complex suture (knot arrangement) can then be tightened in the manner, which will be described below.

The above-described guidance of the thread 60 in particular on the upper jaw section 10 thereby has the result that, in response to this release of the jaw pair from the suture carrier and a cast-off of the thread from the suturing head of the suture end 40 associated therewith is guided through the loop, which is essentially formed by the thread connecting section 62 along the arrow direction 122 in the manner shown in partial Figure (c), and leads to a knotting or an upper web and loop formation, respectively, on the carrier 110 according to the partial images (d) and (e), which represent further tightening states of the thread. The result is the complex knot image of the suture according to FIG. 6 (a), wherein the thread section 102 corresponds to the first piercing D1, the thread section 101 corresponds to the second piercing D2, and the thread section 103 corresponds to the third piercing D3. The tightened loop section 120 has become a firm crossweb structure, which connects the sections 101 and 103 on the underside of the carrier 110, while the middle section 62 has become a deflected upper crossweb and knot structure 124 on the opposite upper side of the carrier. The shown thread end 105 leads to the loop section 63 as first thread end, thread section 104 leads to the second thread end 40 (illustrated without needle 41).

With regard to tear resistance and strain on the suture carrier, the knot created in this way, similarly to the Mason-Allen suture structure known from the medical literature, represents an optimum between tear-out resistance and carrier strain, in particular in the case of biological-medical uses, and is thereby in particular suitable for uses in connection with the fastening of suture material to tendon, ligament or muscle ends or similar highly strained sections.

As compared to the illustration of FIG. 6 (a), the partial Figure (b) represents an opposite flat side of the suture carrier, thus rotated by 180 degrees as compared to the illustration of FIG. 6 (a).

The detail illustrations of FIG. 7 or 8, respectively, additionally described structural or handling-related details, respectively, of the above-described implementation of the suture material handling device according to the invention or of the system realized therewith, respectively. It thus becomes clear in particular by means of the partial Figures (a) to (c), how the thread loop in the connecting section 62 slips (see arrow X in FIGS. 7(a) and (b)) from its holding or guiding position, respectively, on the upper jaw section in the course of the removal of the suturing head with of the pair of jaw sections 10, 20 (thus after the establishing of the state according to partial image (b) in FIG. 5), and is guided into the guide according to partial image (c) of FIG. 5. It in particular becomes clear that the first thread end (loop 63) is held in the lower jaw section 10 after performing the corresponding first piercing D1 and is entrained by it, while the second thread end 40 (comprising end-side needle 41 and corresponding end-side thread section 61) is held in the receiving and entraining elements of assembly 80. As can in particular be seen from a comparison of the partial illustrations (a) to (c) of FIG. 7, the connecting section 62 slips between an upper surface of the carrier section 16 of the upper jaw section and the cropped arm 32 of the pivotable needle element 30, until the loop formation shown in partial Figure (c) of FIG. 7 (thus analogously to FIG. 5 (c)) is created, which, with regard to the partial illustrations (d) and (e) of FIG. 5, can then be tightened by further pulling the head away from the carrier 110.

FIG. 8 additionally clarifies in detail the interaction of the assemblies, whereby the illustration of FIG. 8 describes that operating state (thus analogously to FIG. 5 (b)), in which the curve shank 31 has pierced the carrier 110 for the third piercing again and has brought the second thread end with front-side needle tip 41 into the entraining unit of assembly 80, to which the needle 41 has latched.

The present invention is not limited to the details of the first exemplary embodiment shown in FIGS. 1 to 8. In fact, the sequence of the piercings D1 to D3 is also only preferred, as already specified, and can in particular be varied with regard to the functionally of the first needle elements and the time of the actuation of these first needle elements. The association of the functional aggregates with the upper or lower jaw sections, respectively, is likewise also not defined and can also be reversed, in the same way as, for instance, the functionality of the first needle elements can be reversed (i.e. the first thread end is supplied from below instead of entrained from the top), in the same way as, for instance, the functionality of the second needle elements can be reversed (i.e. the second thread end is entrained only after piercing has occurred and is then also retracted in response to the rearward pivoting, instead of, as described above, being brought to the entrainment receptacle by means of the piercing by the carrier). A possible alternative embodiment of the invention also provides that the bendable flat needle 50, which is provided in the lower jaw section, is not moveably guided in this lower jaw section, for instance, but is rigidly connected to the lower (or upper) jaw section. This rigid needle, which protrudes or sticks out, respectively, with its needle end would thus be moved, together with the movement of the (lower or upper, respectively) jaw section and can be actuated accordingly.

The invention claimed is:

1. A suture material handling device for a thread made from a surgical suture material, the device comprising a suturing head having a first and a second jaw section capable of being pivoted and/or folded relative to one another, and a first needle element associated with the jaw sections and designed for performing a first piercing and a thread entraining operation of a first thread end of the thread in a relative position of the jaw sections that is closed and/or in which the jaw sections have been moved toward one another, further comprising
    a second needle element associated with the jaw sections configured to be actuated separately from the first needle element and provided adjacent to the first needle element and designed to perform a second piercing and a thread entraining operation for a second thread end, which is opposite the first thread end, of the thread in the relative position of the jaw sections that is closed or in which the jaw sections have been moved toward one another, respectively,
    wherein, in order to perform a locally spaced apart and consecutive double piercing of a suture carrier, which can be received between the jaw sections in the relative position that is closed or in which the jaw sections have been moved toward one another, respectively, the second needle element has an entraining section moveable around a longitudinal axis of one jaw of the jaw sections to perform a pivoting and/or curved motion that entrains the second thread end.

2. The device according to claim 1, wherein the second needle element has a curve shank, which embodies the entraining section on an end side for releasably inserting the second thread end.

3. The device according to claim 2, wherein the curve shank is arcuately curved, and wherein the entraining section is designed in a needle-like manner or can carry a needle.

4. The device according to claim 1, wherein the second needle element has a shank assembly comprising a shaft and the curve shank, which is rotatable around an axis of the shaft by way of motor and/or manually.

5. The device according to claim 4, wherein the shank assembly is designed so as to be deflected or cropped, respectively, eccentrically to the entraining section at a transition section.

6. The device according to claim 4, wherein a guide and/or receiving section for the first thread end is formed adjacent to one of the jaw sections for interacting with the first needle element.

7. The device according to claim 4, wherein the shank assembly is rotatably secured to one of the jaw sections.

8. The device according to claim 1, wherein the other jaw of the jaw sections has a guide slit for receiving the entraining section of the second needle element during movement of the entraining section around the longitudinal axis.

9. The device according to claim 1, wherein thread end receiver elements, which are designed such that the second thread end can be inserted therein after the double piercing in a latching or snapping manner, and configured to be released from the entraining section of the second needle element, are associated with at least one of the jaw sections.

10. A system for producing a suture knot in a flat suture carrier having a first and an opposite second flat side and being made of a biological material,
having a suture material handling device according to claim 1, as well as a thread, wherein the handling device further comprises thread guide elements,
wherein
the second needle element has a deflecting element designed such that
a first free end of the thread for forming a first piercing can be brought through the suture carrier from the first to the second flat side,
a second free end of the thread for forming a second piercing adjacent to the first piercing can be brought through the suture carrier from the first to the second flat side,
and then, for forming a third piercing, can be brought through the suture carrier from the second to the first flat side after a deflection of the second free end, which forms a tight and/or tightenable first thread loop on the second flat side,
wherein the first and the second jaw sections are designed so as to be capable of being brought into releasable contact with the first or second flat side, respectively, and a thread section of the thread connecting the first and the second free end on the first flat side can be releasably held in the first and second jaw section such that the connecting thread section can be released from the jaw sections in response to a releasing of the contact after forming the piercings,
and can be tightened on the first flat side by means of a tensile force exerted on at least one of the thread ends for producing a second tight and/or tightenable thread loop on the first flat side.

11. The system according to claim 10, wherein the connecting thread section can be releasably held in the first and/or second jaw section such that the second free end of the thread is guided through the not yet tightened second thread loop in response to the releasing of the contact.

12. The system according to claim 10, wherein a thread end receiver element, which is designed such that the second free end of the thread can be inserted therein after the formation of the third piercing, and can be released from the second needle element, is associated with one of the jaw sections.

13. The system according to claim 12, wherein the second free end can be inserted in a latching or snapping manner.

14. The system according to claim 10, wherein, on the second free end, the thread has a firm abutment section, designed in a needle-like manner, for receiving and guiding by means of the second needle element.

15. The system according to claim 10, wherein, on the first free end, the thread is designed in a loop-like manner and/or comprising an abutment for interaction with the first needle element.

16. The system according to claim 15, wherein the abutment is a flexible abutment.

17. The system according to claim 10, wherein the thread guide elements and the second needle element having the deflecting element can be actuated manually.

18. The device according to claim 1, wherein movement of the jaw sections is by manual actuation.

19. The device according to claim 1, wherein the second needle element is mounted to the one jaw of the jaw sections, and the first needle element is mounted to the other jaw of the jaw sections.

20. The device according to claim 1, wherein the entraining section is moveable around the longitudinal axis between a first position on one side of a gap between the jaw sections, and a second position rotated through the gap and extending back into the one jaw.

* * * * *